United States Patent [19]

Zuber

[11] 4,030,979

[45] June 21, 1977

[54] METHOD OF DETECTING HYDROGEN-PRODUCING BACTERIA

[75] Inventor: Walter Henry Zuber, Stowe, Vt.

[73] Assignee: Walter H. Zuber, Jr., Stowe, Vt.

[22] Filed: Dec. 10, 1975

[21] Appl. No.: 639,457

[52] U.S. Cl. .......................... 195/103.5 M; 195/127
[51] Int. Cl.² .......................................... C12K 1/04
[58] Field of Search ........... 195/103.5 R, 103.5 M; 23/232 R

[56] References Cited

UNITED STATES PATENTS

| | | | |
|---|---|---|---|
| 3,553,082 | 1/1971 | Hach | 195/103.5 R |
| 3,567,383 | 3/1971 | Langley et al. | 23/232 |
| 3,907,646 | 9/1975 | Wilkins et al. | 195/103.5 R |

*Primary Examiner*—Alvin E. Tanenholtz
*Attorney, Agent, or Firm*—Jonathan Meyers

[57] ABSTRACT

The presence of bacteria capable of producing hydrogen in a culture medium is determined by qualitatively and quantitatively detecting hydrogen by subjecting the culture medium to a hydrogen-sensing device and qualitatively and quantitatively redetecting hydrogen by resubjecting the culture medium to the hydrogen-sensing device.

12 Claims, 1 Drawing Figure

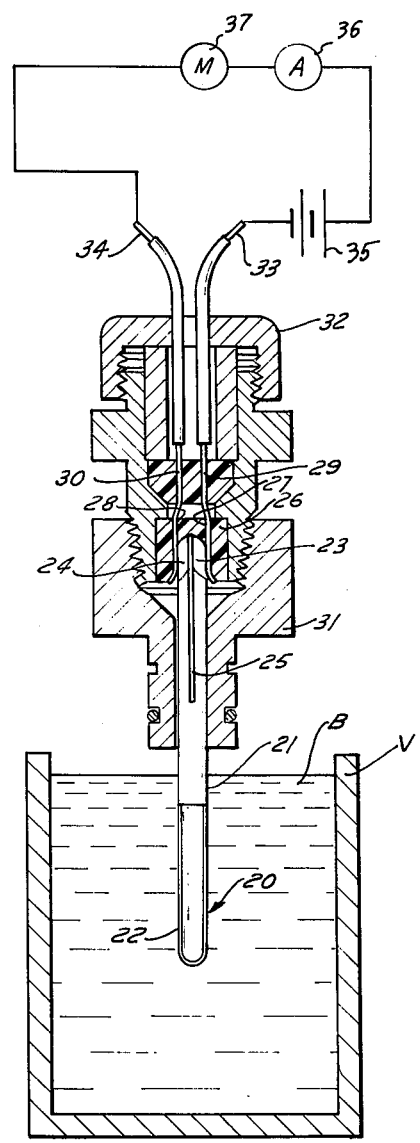

METHOD OF DETECTING HYDROGEN-PRODUCING BACTERIA

FIELD OF THE INVENTION

This invention relates to a method of detecting bacteria capable of producing hydrogen in a culture medium. More particularly, the invention relates to the detection of the hydrogen gas produced by the bacteria by determining a change in the amount of hydrogen present in a culture solution suspected of containing such bacteria, especially *E. coli*.

BACKGROUND OF THE INVENTION

Pollution of water with fecal material, whether infected or not, is obviously undesirable, both from the standpoint of its possible danger as a source of infection and for purely esthetic reasons. The detection in water of fecal bacteria of any kind is therefore of importance in determining its suitability for drinking purposes. One very common, readily cultivated and numerically predominant type of intestinal organism is the *Escherichia coli* (*E. coli*). In the United States *E. coli* is considered a sensitive indicator of pollution.

In order to determine its presence, advantage is taken of the ability of *E. coli* to ferment lactose with the production of gas. But, the Aerobacter and also *E. freundii* ferment lactose with gas production and it is therefore of importance to distinguish between the three because *E. coli* is definitely an intestinal organism while Aerobacter and *E. freundii* are also frequently derived from soil.

The American Public Health Association has outlined an official procedure for the isolation of Escherichia and Aerobacter from water and has described an unofficial but useful procedure for the differentiation between *E. coli* of truly intestinal nature and closely related, but less frequently intestinal, organisms like *E. freundii* and the Aerobacter. Briefly, the procedure is as follows:

The water to be examined is inoculated in measured amounts into tubes of extract 0.5% lactose broth, and is incubated for 24 hours. If gas is formed it is regarded as presumptive evidence that *E. coli* is present.

However, the gas may be due to Aerobacter or other organisms such as *Clostridium perfringens*, yeasts or synergistic combinations capable of producing gas from lactose. The broth culture is streaked in an agar medium containing some dye which inhibits all but the Escherichia and Aerobacter. If, after inoculation of these liquid cultures, gas is produced, it is strongly suggestive of the presence of Aerobacter or or Escherichia because most other species are inhibited by the dyes. The liquid dye cultures may, for further proof, be streaked on the dye-containing plates as mentioned above. Finally, addition tests are made, to distinguish the Aerobacter from the Escherichia, and *E. coli* from *E. freundii*. See Frobisher: Fundamentals of Bacteriology, pp. 431–453, W. B. Saunders Co. (Philadelphia 1944).

The shortcomings of this method are the long time of fermentation needed to get results (particularly for samples which contain small amounts of bacteria, the usual case), the need for visual observation and complicated laboratory procedure. In a typical testing laboratory, hundreds of thousands of samples are run daily.

In the prior art, there have been various approaches to decrease monitoring time and to make monitoring automatic. One prior art method teaches use of impedance changes within the medium to measure growth of various bacteria. Any changes in the electrical resistance between two electrodes in the culture medium are related to the amount of bacteria present. More information on this subject may be found in *Impedance Changes in Media as a Method of Identifying Microorganisms*, Lawless, Dufour and Cady; Bactomatic, Inc.; Palo Alto, Cal.; 1973.

Another approach is to use isotope labelling of the nutrient medium. For example, if a sugar containing some carbon-14 is used as a nutrient, bacteria present will metabolize the sugar and produce labeled carbon dioxide. The instrument determines the presence and measures the amount of the isotope in the atmosphere above the culture. This technique is more fully described in U.S. Pat. No. 3,676,679.

A third approach is to continuously circulate the culture media through a glass tube and measure changes in turbidity as bacteria multiply.

However, each of the above methods has the disadvantage of either taking a good deal of time or requiring expensive equipment or both.

OBJECT OF THE INVENTION

It is the object of this invention to provide a rapid, inexpensive, sensitive method of detecting the presence and amount of bacteria capable of producing elemental hydrogen in a culture medium.

SUMMARY OF THE INVENTION

Many bacteria which pollute the Nation's water supplies give off hydrogen (both diatomic and nascent) which is a tell-tale indication of the bacteria's presence. Surprisingly, this tell-tale hydrogen can be determined both quantitatively and qualitatively so as to warn ecologists and health officials of the danger in a simpler manner than practiced heretofore. I have found that by culturing a sample of water suspected of containing hydrogen-producing bacteria (said culturing accomplished by known means) I can qualitatively and quantitatively determine the hydrogen emitted by these bacteria. I determine the amount of hydrogen present in the untreated sample and compare this reading after the sample has been cultured and some time has elapsed (often as little as 24 hours or less). An increase in the amount of hydrogen detected in the second reading indicates the presence of the hydrogen producing bacteria.

Any conventional method of detecting hydrogen may be employed in my invention. One preferred method is by the use of mass spectroscopy. A method even more preferable includes making at least two measurements of an electromagnetic parameter of a supported palladium oxide thin film which is easily reduced by any present hydrogen.

By immersing the palladium oxide probe of a conventional detector for hydrogen in the atmosphere into a cultured solution suspected of containing elemental hydrogen-producing bacteria, a rapid change in an electromagnetic parameter of the probe will occur if indeed there are bacteria present. A dramatic change in the parameter's value can occur in as little as 24 hours which is considerably more rapid than the time required in the prior art.

I can carry out my process under various ambient conditions, but prefer to do so at about 36° to 37° and under aerobic conditions. These conditions require a minimum of effort to effect and maintain. Also, while any change of several electromagnetic parameters of the palladium oxide will accurately indicate the presence of elemental hydrogen. I prefer to measure either its resistivity or reflectivity.

For quantitative estimation of a hydrogen producing bacteria titer, standard dilutions of known concentrations of hydrogen-producing bacteria in appropriate culture medium are contacted with the subject hydrogen detector and the time for each dilution to produce a predetermined or standard reflectivity or resistivity change is recorded and charted. One or more dilutions of an unknown sample containing suspected hydrogen-producing bacteria are introduced into a fresh culture medium of the same composition as the standards and are likewise contacted with the subject hydrogen probe. The time to produce the standard change in reflectivity or resistivity is noted and compared with the data of the standard chart to give the original concentration of hydrogen producing bacteria in the unknown sample.

Another feature of my invention is that an alarm system is activated should the electromagnetic parameter under-going measurement show a change. Therefore, an operator need not constantly observe a meter or other measuring device. Such alarm systems include both light- and sound-producing devices.

Yet another feature of my invention is that the determination of a change in the electromagnetic parameter undergoing measurement is made prior to the formation of any gas bubbles. If elemental hydrogen is present within the culture medium, such bubbles will often appear after some time has elapsed. However, even where such bubbles are not apparent because the amount of hydrogen present is too little to form noticeable bubbles, my system can detect any elemental hydrogen present.

The detector which I prefer to use is disclosed in U.S. Pat. No. 3,567,383 issued to Langley et al. This patent discloses an apparatus for detecting the presence of hydrogen in a mixture of gases. The detector has a probe with a very thin film of palladium oxide (250 to 500 Angstroms). This film is light tan and transparent. In the presence of hydrogen at room temperature, the film rapidly changes to metallic palladium with a large change in electromagnetic properties. The film becomes opaque, reflective, and metallic gray. The palladium oxide film is also a semiconductor with a high but easily measured electrical resistivity at room temperature. In the presence of hydrogen, the film is reduced to a metal with a very large decrease in electrical resistance. This change can be determined by using the palladium oxide film as a resistor in an electrical circuit.

Since the detector is portable and inexpensive to own and operate, my process will also have these advantages. I wish to point out, however, that no use of this detector has been effected or even suggested by the prior art for the detection of elemental hydrogen or hydrogen-producing bacteria in a liquid medium.

I wish to clarify and define the term "hydrogen-detection" with regard to the Langley-Rubin detector. Although not fully known at this time, it is assumed that change in physical properties of the detector's probe during growth of bacteria was due to the presence of hydrogen. As can be seen from the examples included hereinafter, the detector's probe also undergoes marked change after very brief exposure to thiosulfate ion.

BRIEF DESCRIPTION OF THE DRAWING

The above and other objects, features, and advantages will become more readily apparent from the following, reference being made to the accompanying drawing whose sole FIGURE shows an apparatus for the process according to the present invention.

SPECIFIC DESCRIPTION

The drawing shows an apparatus using a probe 20 which has a rod 22 which is 0.125 inches in diameter and 4.0 inches long and described in U.S. Pat. No. 3,567,383. This probe has a palladium oxide film 21/500 A thick covering its entire surface except for a region 25, subdividing the upper end of the sensor 20 into two terminals 23 and 24. The rod 22 is mounted in a nylon socket having two holes 27 and 28 receiving detector wires 29 and 30 and screwed into a fitting 31 of the "Gra-Tec" quick-connect type. This fitting 31 is itself mounted in a "Conax" connector 32 which has leads 33 and 34 connected to the wires 29 and 30. A battery 35, alarm 36, and indicator or meter 37 are connected in series between the leads 33 and 34.

The sensor 20 is sterilized and immersed in a container or vessel V containing a bath B in which is provided an inoculated culture medium. The meter 37 will indicate the presence of elemental hydrogen and the alarm 36 will operate when a predetermined level is exceeded.

EXAMPLE 1

Sensors were prepared by a modification of the method described in Example 1 of U.S. Pat. No. 3,567,383. A solution containing 2% Pd by weight was made by diluting a commercially available palladium resinate solution with a mixture of oil of Rosemary chloroform and nitrobenzene. The solution was applied by brushing to flat alumina ceramic chips, 2.5 × 2.5 cm in size. The coated area was approximately 2.5 × 1.0 cm in size. The chips were fired in air to 550° C and strongly adherent light orange films of palladium oxide were obtained. These were approximately 250 to 500 Angstroms in thickness.

For convenience in measuring electrical resistance of the films, heavy lines were drawn over each end of the sensor strips with a soft lead pencil and these lines were used for making contact with the probes of a Triplett Model 630 ohm-meter. Resistance values varied from sensor to sensor due to differences in the coated areas between the contacts. All resistances were high, with a range of 165,00 to 650,00 ohms.

EXAMPLE 2

Sensors were tested by immersion in 0.1N hydrochloric acid. There was no optical change in the palladium oxide film and no change in electrical resistivity after 2 hours exposure. A similar test using 0.1N sodium hydroxide for 2 hours also produced no change in physical properties of the sensor film.

A sensor exposed to hydrogen gas for 1 hour changed from an initial value of 290,000 ohms to 2,500 ohms. In addition, the original light orange color of the sensor film changed to opaque metallic gray, the characteristic appearance of metallic palladium. Associated with these changes was a decrease in adherence of the film.

This may be due to stress in the metallic film when saturated with hydrogen.

A sensor was immersed in a dilute aqueous solution of sodium thiosulfate. After 5 minutes, electrical resistance had changed from an initial value of 430,000 ohms to 3,200 ohms. The film changed to opaque metallic gray from its original, light orange color.

EXAMPLE 3

Three cultures were selected from the American type Culture Collection as typical of the bacteria commonly found in contaminated water supplies. These cultures were *Streptococcus faecalis* (ATCC 19433), *Escherichia coli* (ATCC 4157) and the *Proteus vulgaris* (ATCC 8427). *S. faecalis* was grown in liquid culture in Difco Brain Heart Infusion Broth. *E. coli* and *P. vulgaris* were each grown in Difco Nutrient Broth, all at 37° C.

In all three cultures, the sensor films were observed to have changed to opaque, metallic appearance after 24 hours exposure. This optical change was relatively more pronounced in the case of *S. faecalis* and *P. vulgaris*.

In another experiment, a sensor was measured before immersion in a culture of *P. vulgaris* and found to have electrical resistance of 165,000 ohms. After 24 hours immersion this value had changed to 3,550 ohms. The characteristic appearance of metallic palladium was also observed in this sensor film after the 24 hour period.

In control experiments, sensors were immersed in the two growth media, not containing bacteria, for a period as long as 72 hours. There was no decrease in electrical resistivity of these sensors and no significant optical change was observed.

EXAMPLE 4

Raw sewage from a domestic septic system was diluted with water. These samples were then mixed with a nutrient solution (Difco Nutrient Broth) and the mixture was bottled and maintained at 98° F. A Langley-Rubin sensor in the form of a thin palladium oxide film on an alumina ceramic substrate was immersed in the solution. A pronounced optical change was observed in the sensor film in about 45 minutes. However, no change occurred where the nutrient solution was run alone.

I claim:

1. A method of detecting the presence of bacteria capable of producing hydrogen in a liquid culture medium which comprises the following steps:
   a. qualitatively and quantitatively detecting hydrogen by subjecting the liquid culture medium to a hydrogen-sensing device;
   b. qualitatively and quantitatively redetecting hydrogen by resubjecting the liquid culture medium to the hydrogen-sensing device of step (a) sometime thereafter; and
   (c) relating any change in the hydrogen concentration to bacterial content.

2. The method defined in claim 1 wherein the hydrogen is detected by determining a change in the value of an electromagnetic parameter of a supported palladium oxide thin film.

3. A method of detecting the presence of bacteria capable of producing hydrogen in a liquid culture medium which comprises the following steps:
   a. immersing a supported thin film of palladium oxide into the culture medium;
   b. determining an electromagnetic parameter of the supported palladium oxide thin film at the time of the initial immersion into the liquid culture medium in step (a);
   c. redetermining the electromagnetic parameter of the supported palladium oxide thin film subsequent to step (b) during an incubation period; and
   d. relating any change in the hydrogen concentration to bacterial content.

4. The method defined in claim 3 wherein the temperature of the culture medium is about 36° C.

5. The method defined in claim 3, step (b) wherein the electromagnetic parameter is sheet resistivity.

6. The method defined in claim 3, step (b) wherein the electromagnetic parameter is reflectivity.

7. The method defined in claim 3, step (a) wherein the thin film has a thickness of between 250 and 500 A. and is supported on a dielectric substrate.

8. The method defined in claim 3 wherein the culture medium is calibrated against a culture medium with a known bacteria content to allow quantitative determination of the elemental hydrogen producing bacteria.

9. The method defined in claim 3 wherein the time that elapses between step (b) and step (c) is about 1 day.

10. The method defined in claim 3, step (c) wherein an alarm system is activated if the electromagnetic parameter is different from the one in step (b).

11. The method defined in claim 3 wherein step (c) is carried out prior to the formation of any visible gas bubbles.

12. The method defined in claim 3 wherein the bacteria capable of producing elemental hydrogen is *E. coli* and the culture medium is Difco Nutrient medium.

* * * * *